United States Patent [19]
Bucalo et al.

[11] Patent Number: 5,857,981
[45] Date of Patent: Jan. 12, 1999

[54] BIOPSY INSTRUMENT WITH TISSUE SPECIMEN RETAINING AND RETRIEVAL DEVICE

[76] Inventors: Brian D. Bucalo, 1010 S. Ocean Blvd., #LPH9, Pompano, Fla. 33062; Louis R. Bucalo, 3418 Pivijadevo St., San Francisco, Calif. 94123

[21] Appl. No.: 527,257

[22] Filed: Sep. 12, 1995

[51] Int. Cl.[6] ................................................. A61B 10/00
[52] U.S. Cl. ........................................... 600/562; 600/581
[58] Field of Search ..................................... 128/749–755

[56] References Cited

U.S. PATENT DOCUMENTS

| | | | |
|---|---|---|---|
| 2,839,049 | 6/1958 | MacLean | 128/756 |
| 4,785,826 | 11/1988 | Ward | 128/754 |
| 5,148,813 | 9/1992 | Bucalo | 128/754 |
| 5,267,572 | 12/1993 | Bucalo | 128/754 |
| 5,423,330 | 6/1995 | Lee | 128/753 |

*Primary Examiner*—Max Hindenburg
*Assistant Examiner*—Pamela L. Wingood
*Attorney, Agent, or Firm*—Steinberg & Raskin, P.C.

[57] ABSTRACT

A biopsy instrument including a tissue penetrating device including an elongate holder and a cutting member arranged at an end thereof for penetrating tissue and a specimen retaining and retrieval device detachably connected to the holder for receiving and retaining a specimen of tissue cut by the cutting member. The specimen retaining and retrieval device preferably has a handle having a contoured, outer surface substantially corresponding to the shape of a thumb and which is roughened. Also, preferably the tissue penetrating device includes a hand grip section arranged at an end of the holder opposite to the end at which the cutting member is arranged and a middle section arranged between the hand grip section and the cutting member, the middle section being substantially cylindrical and having friction grip enhancing means, i.e., grooves arranged on an outer peripheral surface in a direction substantially perpendicular to the longitudinal direction of the tissue penetrating device.

16 Claims, 3 Drawing Sheets

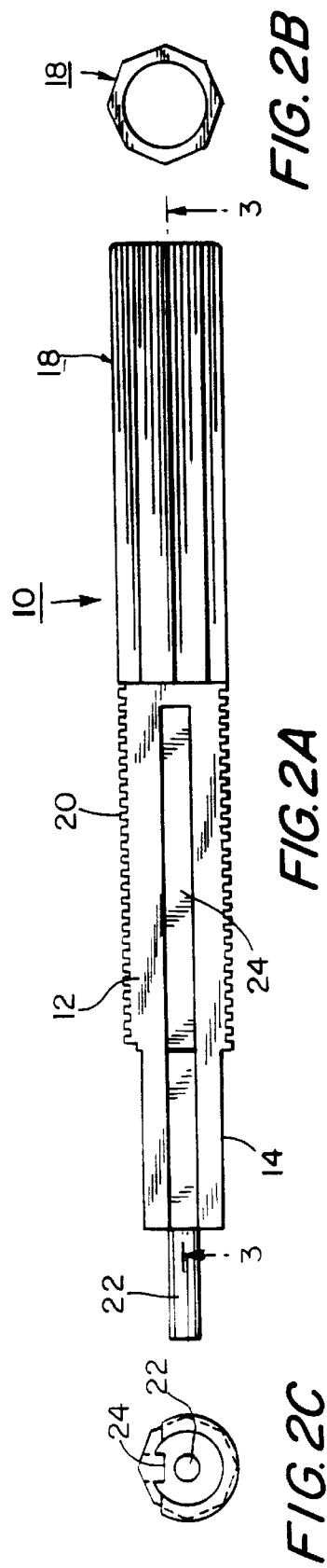
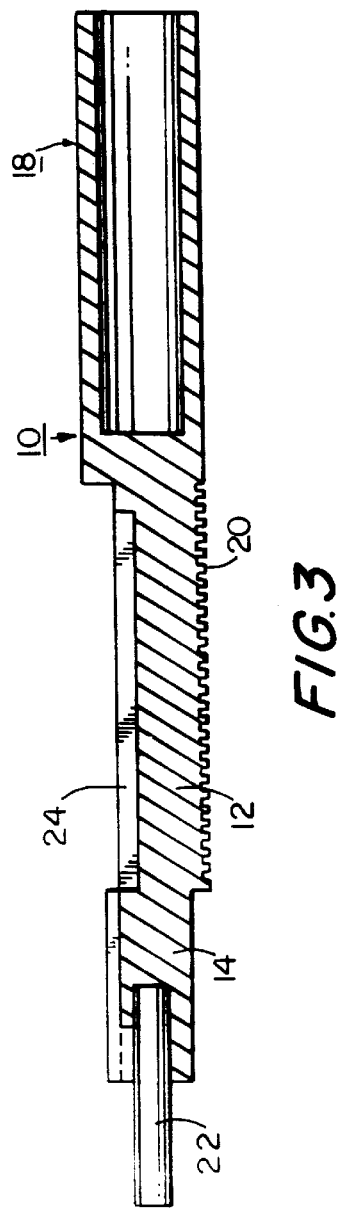

FIG. 4
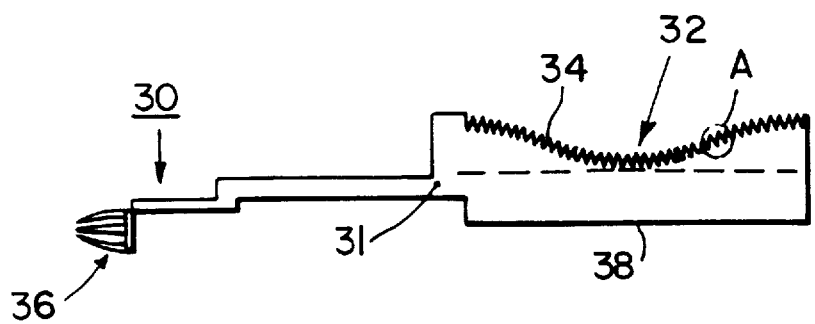
FIG. 4A
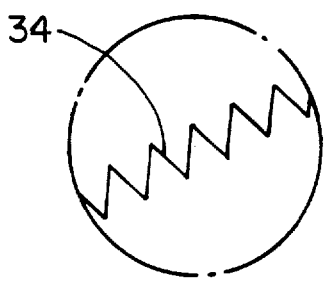
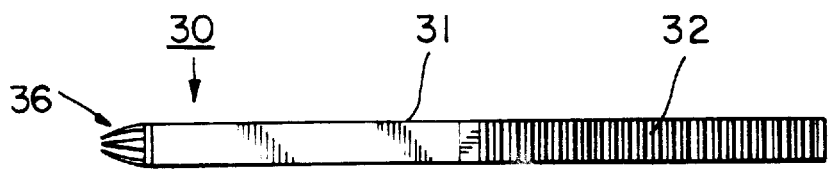
FIG. 5

BIOPSY INSTRUMENT WITH TISSUE SPECIMEN RETAINING AND RETRIEVAL DEVICE

BACKGROUND OF THE INVENTION

The present invention relates to biopsy instruments used for collecting specimens of tissue from the skin of internal organs for subsequent analysis. The invention particularly relates to skin punch biopsy devices which are conventionally used to bore cylindrical channels in the skin by rotating a tubular cutting sleeve to advance the sleeve into tissue.

A serious problem which has occurred with conventional punch type biopsy instruments is that these instruments are incapable of separating the tissue specimen from the surrounding tissue once the rotational cutting action has been completed. Almost invariably, as the biopsy instrument is withdrawn, the tissue specimen remains attached to the body at the uncut portion of its base and must then be lifted with a needle point or tweezers and the attached base portion excised with a scalpel blade. This secondary operation is not only tedious and time consuming but also requires additional equipment in the form of a scalpel and unnecessarily places medical personnel at risk for such infectious diseases as hepatitis and AIDS through accidental needle punctures, scalpel cuts, or blood splashes. Also, this secondary removal operation is very difficult to perform on agitated human patients or on unwieldy animals.

An additional problem which arises with conventional skin punch biopsy instruments concerns the fact that the collected biopsy specimens are normally placed in a vial containing preservative solution. Thus, specimens which are small in size are often difficult to find and retrieve, especially if the preservative solution has been darkened with blood or other body fluids from the specimen.

One additional problem which has arisen with conventional biopsy punch instruments is that they are difficult to grasp, especially due to longitudinal grooves which are often molded in the handle.

One attempt to solve some of the above-mentioned problems is found in U.S. Pat. No. 4,785,826, issued to Ward. This patent discloses a biopsy needle having a first hollow member with a second elongated hollow member fitted within the first hollow member. The second member has a flexible end portion included pointed segments which are normally opened to receive a tissue specimen, and which can be closed by moving the inner member axially with respect to the outer member (by means of twisting one with respect to the other). The tapered segments are deformed by a shoulder formed on the inner surface of the outer member, thereby being bent inwardly to cut and capture a tissue specimen.

Another attempt to solve some of the above mentioned problems is found in U.S. Pat. Nos. 5,148,813 and 5,267,572. These patents describe biopsy instruments with tissue specimen retaining and retrieval devices. However, these instruments suffer from the same drawbacks as previous inventions in that they are difficult to grasp during use. These patents also provide a more comprehensive explanation of the use of a biopsy instrument having a tissue penetrating device and a specimen retaining and retrieval device detachably connected to the tissue penetrating device and therefore are incorporated by reference herein.

OBJECTS AND SUMMARY OF THE INVENTION

Accordingly, one object of the present invention is to provide a biopsy instrument which efficiently removes tissue specimens and which provides efficient contact with and retrieval from preservative solutions.

A primary object of the present invention is to provide a new and improved biopsy instrument which is easier to grasp than prior art devices and conforms to the contours of the hand and fingers.

Another object of the present invention is to provide a new and improved biopsy instrument which has located along its outside surface a removable, tissue specimen retaining and retrieval means incorporating a series of barbs which engage the specimen and remove it from the surrounding tissue when the biopsy instrument is withdrawn.

Still another object of the present invention is to provide a biopsy instrument which will rapidly and easily lift the biopsy specimen from the surrounding tissue and eliminate the need for manual lifting and excision of the biopsy tissue specimen, thereby saving time, equipment costs, and preventing the exposure of health care personnel to the hazards of blood borne infections, as well as reducing the time required for removal of a tissue specimen from agitated patients or unwieldy animals.

Yet another object of the present invention is to provide a tissue specimen retaining device comprising a combination of a specimen retaining means and a handle to provide greater flexibility in connection with transporting the biopsy tissue specimen to the preservative solution providing for efficient contact with the preservative, and in retrieving the tissue specimen therefrom.

A still further object of the present invention is to provide a biopsy instrument that may be operated to collect a tissue specimen while requiring utilization of only one hand of the operator.

These and other objects are attained in accordance with the present invention by providing an improved biopsy instrument which comprises a detachable tissue specimen retaining and retrieval device which device utilizes a plurality of barbs to sever a tissue specimen from a volume of tissue into which the biopsy instrument has bored, and which device also has a handle which is detachable from the rest of the biopsy instrument such that the device holding the severed tissue specimen can easily be transferred to and removed from a preservative solution, or other tissue treatment process and analysis. The tissue retaining and retrieval device, although generally rotatable relative to the tissue penetrating means of the conventional biopsy instrument, contains means for preventing this relative rotation.

In one preferred embodiment of the invention, the tissue specimen retaining and retrieval device comprises a handle with a sleeve integrally attached to the handle and located so as to surround the cylindrical cutting member of the biopsy instrument as it bores into tissue and barbs integral with one end of the sleeve and exerting a radially inward pressure on the cylindrical cutting member. The handle has a curved end surface which is shaped so as to conform to the contours of the thumb and preferably includes ridges or projections so as to provide for increased friction between the handle and the thumb.

The biopsy instrument, and more particularly the tissue penetrating device portion thereof, has on at least a portion of its surface a friction grip which prevents the fingers of the user from sliding in a direction parallel to the longitudinal axis of the biopsy instrument. This friction grip may be in the form of a knurled surface or circumferentially cut parallel grooves. A cylindrical cutting member is attached to one end of the biopsy instrument.

BRIEF DESCRIPTION OF THE DRAWINGS

A more complete appreciation of the present invention and many of the attendant advantages thereof can be readily understood by reference to the following detailed description when considered in connection with the accompanying drawings in which:

FIG. 2A is a side view of the tissue penetrating device in the biopsy instrument in accordance with the invention;

FIG. 2B is a front view of the biopsy instrument shown in FIG. 2A;

FIG. 2C is a rear view of the biopsy instrument shown in FIG. 2A;

FIG. 3 is a cross-sectional view taken along the line 3—3 in FIG. 2A;

FIG. 4 is a side view of a handle which forms the tissue specimen retaining and retrieval means in the biopsy instrument in accordance with the invention;

FIG. 4A is an enlarged view of the detail A as shown in FIG. 4; and

FIG. 5 is a top view of the handle shown in FIG. 4.

DESCRIPTION OF THE PREFERRED EMBODIMENTS

Figure 1:
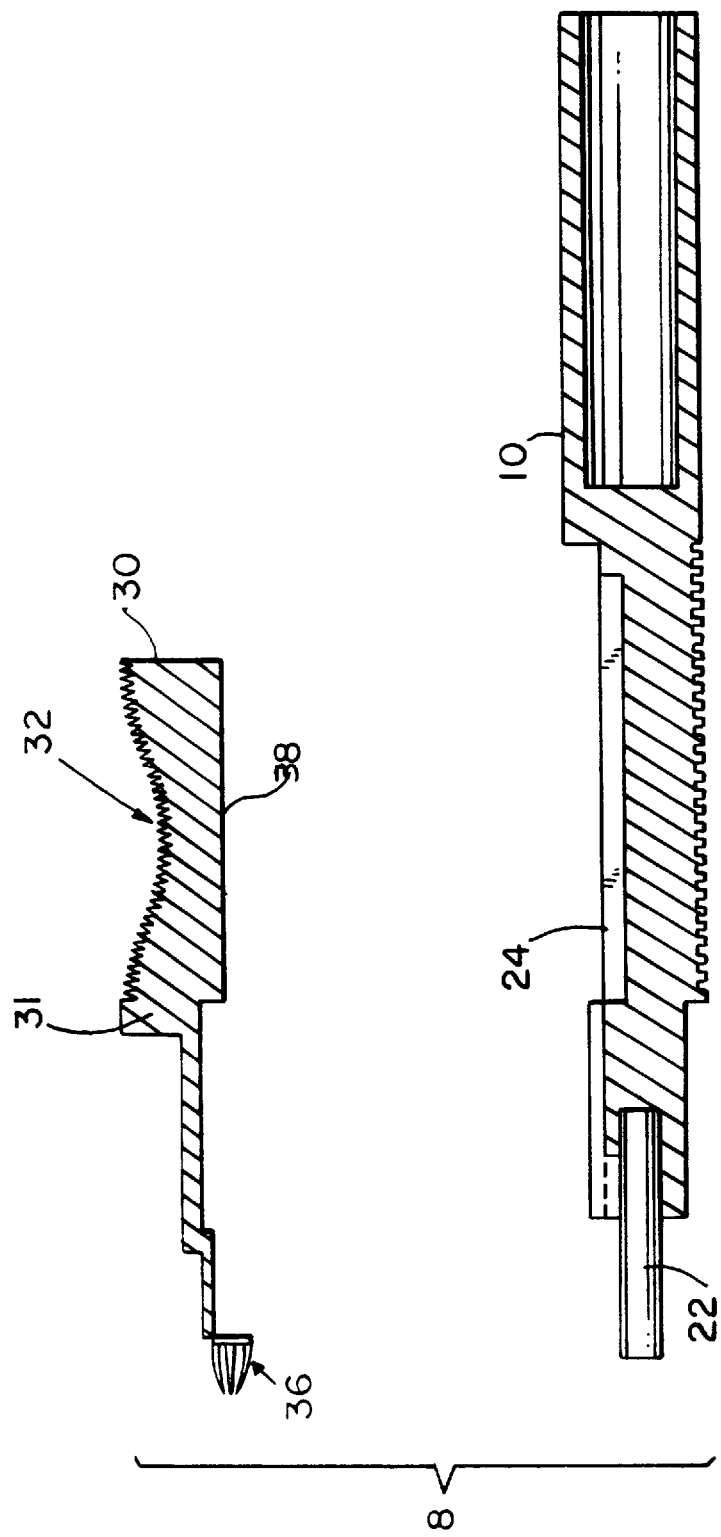
FIG. 1 is an exploded sectional view of the biopsy instrument in accordance with the invention.

Referring to the accompanying drawings wherein the same reference numerals designate the same or similar elements, as shown in FIG. 1, a biopsy instrument, generally designated 8, comprises a tissue penetrating device 10 and a specimen retaining and retrieving device 30. In use, the specimen retaining and retrieving device 30 is attached to the tissue penetrating device 8 such that when the biopsy instrument 8 enters an area of tissue, the specimen retaining and retrieving device 30 functions to sever and grasp a specimen of tissue for subsequent analysis.

FIGS. 2A, 2B, 2C and 3 show the tissue penetrating device 10 in greater detail. The tissue penetrating device 10 is elongate and has a hand grip section 18 having a polygonal cross-sectional shape, e.g., octagonal as seen most clearly in FIG. 2B, against which the hand of the doctor performing the biopsy is placed. At an end 14 of the tissue penetrating device 10 opposite the hand grip section 18, cutting means is arranged. The cutting means may be a tubular cutting member 22 having a forward cutting edge for penetrating tissue. In a middle section between the end 14 at which the cutting means 22 is arranged and the hand grip section 18, the middle section 12 has a longitudinal slot or groove 24 arranged in a direction of the axis of the tissue penetrating device 10. Further, around the middle section 12, in areas other than in the slot 24, grooves 20 are arranged. Grooves 20 are preferably parallel grooves and extend circumferentially around the middle section 12, except for in the area of the slot 24. Circular circumferential grooves 20 provide an excellent friction grip which preventing the fingers of the operator from sliding in a direction parallel to the longitudinal axis of the biopsy instrument 8 during use. Longitudinal groove 24 is located in the center line of the device and forms a trough where the specimen retaining and retrieval device is located, as discussed below.

FIGS. 4 and 5 illustrate the specimen retaining and retrieval device 30 used in the biopsy instrument in accordance with the invention for receiving and retaining a specimen of tissue. The specimen retaining and retrieving device 30 comprises an elongate handle 31 incorporating a contoured thumb grip 32 at one end and a plurality of flexible barbs 36 at an opposite end. The thumb grip 32 is shaped so as to conform to the general shape of a human thumb, i.e., depressed in a central region and gradually sloping upward from the central depression. Further, the thumb grip 32 has a roughened upper surface 34, obtained by the placement of roughenings such as ridges or projections, on at least a portion thereof, but not necessarily the entire upper surface, and for example, in a direction transverse to the longitudinal direction of the tissue specimen retaining and retrieving device 30. The handle 31 is constructed so that its lower surface 38 rests in the groove 24 in the tissue penetrating device 10 when the biopsy instrument is assembled (see FIG. 1) and also the barbs 36 overlie the cutting member 22.

The examples provided above are not meant to be exclusive. Many other variations of the present invention would be obvious to those skilled in the art, and are contemplated to be within the scope of the appended claims. As noted above, additional details of the general construction of a biopsy instrument having a tissue penetrating device and a detachable specimen retaining and retrieving device coupled thereto are set forth in U.S. Pat. Nos. 5,148,813 and 5,267,762, which are incorporated by reference herein.

We claim:

1. A biopsy instrument, comprising
   a tissue penetrating device including an elongate holder, first cutting means arranged at an end of said holder for penetrating tissue and a middle section having an outer peripheral surface and including a longitudinal channel recessed inwardly of said outer peripheral surface, and
   a specimen retaining and retrieval device detachably connected to said holder for receiving and retaining a specimen of tissue cut by said first cutting means,
   said specimen retaining and retrieval device comprising
      a handle having a contoured, outer surface substantially corresponding to the shape of a thumb such that said handle of said specimen retaining and retrieval device is fittingly matable with the thumb of the user during penetration and cutting of tissue and said specimen retaining and retrieval device is carryable by the user through the mating of the thumb of the user and said handle upon detachment from said tissue penetrating device, and
      a longitudinal projection extending outward from a bottom surface thereof corresponding in size and shape to said longitudinal channel in said middle section of said tissue penetrating device such that said projection of said specimen retaining and retrieval is insertable into said longitudinal channel.

2. The biopsy instrument of claim 1, wherein said specimen retaining and retrieval device is elongate and comprises second cutting means, said second cutting means comprising a set of barbs mounted at a front end of said specimen retaining and retrieval device and formed to exert a radially inward pressure from said front end.

3. The biopsy instrument of claim 1, wherein said tissue penetrating device comprises a hand grip section arranged at an end of said holder opposite to said end at which said first cutting means are arranged, said middle section being arranged between said hand grip section and said cutting means, said middle section having friction grip enhancing means comprising circumferential grooves arranged on an outer peripheral surface of said middle section and oriented in a direction substantially perpendicular to the longitudinal direction of said tissue penetrating device.

4. The biopsy instrument of claim 3, wherein said tissue penetrating device has a varying cross-section shape along its longitudinal axis, said hand grip section having a polygonal cross-sectional shape.

5. The biopsy instrument of claim 1, wherein said first cutting means comprise a tubular cutting member having a forward cutting edge for penetrating tissue.

6. The biopsy instrument of claim 1, wherein said outer peripheral surface of said middle section of said tissue penetrating device is cylindrical.

7. The biopsy instrument of claim 1, wherein said contoured surface is roughened.

8. The biopsy instrument of claim 1, wherein said contoured surface has a depressed central region and sloping portions gradually sloping upward from said central region.

9. A biopsy instrument, comprising a tissue penetrating device including an elongate holder and first cutting means arranged at an end of said holder for penetrating tissue, said tissue penetrating device comprising a hand grip section arranged at an end of said holder opposite to said end at which said first cutting means are arranged and a middle section arranged between said hand grip section and said cutting means, said middle section being substantially cylindrical and having friction grip enhancing means, said friction grip enhancing means comprising circumferential grooves arranged on an outer peripheral surface of said middle section and oriented in a direction substantially perpendicular to the longitudinal direction of said tissue penetrating device, said middle section having an outer peripheral surface and including a longitudinal channel recessed inwardly of said outer peripheral surface, and a specimen retaining and retrieval device detachably connected to said middle section of said holder for receiving and retaining a specimen of tissue cut by first cutting means, said specimen retaining and retrieval device comprises a longitudinal projection extending outward from a bottom surface thereof corresponding in size and shape to said longitudinal channel in said middle section of said tissue penetrating device such that said projection of said specimen retaining and retrieval is insertable into said longitudinal channel of said tissue penetrating device.

10. The biopsy instrument of claim 9, wherein said tissue penetrating device has a varying cross-section shape along its longitudinal axis, said hand grip section having a polygonal cross-sectional shape.

11. The biopsy instrument of claim 9, wherein said specimen retaining and retrieval device is elongate and comprises second cutting means, said second cutting means comprising a set of barbs mounted at a front end of said specimen retaining and retrieval device and formed to exert a radially inward pressure from said front end.

12. The biopsy instrument of claim 9, wherein said first cutting means comprise a tubular cutting member having a forward cutting edge for penetrating tissue.

13. The biopsy instrument of claim 9, wherein said outer peripheral surface of said middle section of said tissue penetrating device is cylindrical.

14. The biopsy instrument of claim 9, wherein said specimen retaining and retrieval device comprises a handle having a contoured surface substantially corresponding to the shape of a thumb.

15. The biopsy instrument of claim 14, wherein said contoured surface is roughened.

16. The biopsy instrument of claim 14, wherein said contoured surface has a depressed central region and sloping portions gradually sloping upward from said central region.

* * * * *